(12) United States Patent
Lavrentyev et al.

(10) Patent No.: US 10,562,288 B2
(45) Date of Patent: Feb. 18, 2020

(54) ADDITIVE MANUFACTURING SYSTEM WITH ULTRASONIC INSPECTION AND METHOD OF OPERATION

(71) Applicant: United Technologies Corporation, Farmington, CT (US)

(72) Inventors: Anton I. Lavrentyev, Cromwell, CT (US); Alexander Staroselsky, Avon, CT (US); Sergey Mironets, Charlotte, NC (US)

(73) Assignee: United Technologies Corporation, Farmington, CT (US)

( * ) Notice: Subject to any disclaimer, the term of this patent is extended or adjusted under 35 U.S.C. 154(b) by 582 days.

(21) Appl. No.: 15/108,977

(22) PCT Filed: Jan. 15, 2015

(86) PCT No.: PCT/US2015/011610
§ 371 (c)(1),
(2) Date: Jun. 29, 2016

(87) PCT Pub. No.: WO2015/109096
PCT Pub. Date: Jul. 23, 2015

(65) Prior Publication Data
US 2016/0325541 A1    Nov. 10, 2016

Related U.S. Application Data

(60) Provisional application No. 61/928,758, filed on Jan. 17, 2014.

(51) Int. Cl.
*B33Y 40/00* (2015.01)
*B23K 26/342* (2014.01)
(Continued)

(52) U.S. Cl.
CPC .......... *B33Y 40/00* (2014.12); *B23K 15/0026* (2013.01); *B23K 15/0086* (2013.01);
(Continued)

(58) Field of Classification Search
None
See application file for complete search history.

(56) References Cited

U.S. PATENT DOCUMENTS

2004/0173946 A1    9/2004  Pfeifer et al.
2007/0044562 A1    3/2007  Sarr
(Continued)

FOREIGN PATENT DOCUMENTS

WO    WO-2012-097799 A2 *   7/2012
WO    WO2012097799 A2       7/2012

OTHER PUBLICATIONS

Machine translation of WO-2012-097,799-A2, Sep. 2018.*
Machine translation of WO-2012/097,799 A2, Mar. 2019. (Year: 2019).*

(Continued)

*Primary Examiner* — Geoffrey S Evans
(74) *Attorney, Agent, or Firm* — Getz Balich LLC

(57) ABSTRACT

An additive manufacturing system includes an ultrasonic inspection system integrated in such a way as to minimize time needed for an inspection process. The inspection system may have an ultrasonic phased array integrated into a build table for detecting defects in each successive slice of a workpiece and such that each slice may be re-melted if and when defects are detected.

8 Claims, 4 Drawing Sheets

(51) Int. Cl.
  *B23K 26/03* (2006.01)
  *B33Y 10/00* (2015.01)
  *B33Y 50/02* (2015.01)
  *G01N 29/26* (2006.01)
  *B33Y 30/00* (2015.01)
  *B23K 26/70* (2014.01)
  *B23K 15/00* (2006.01)
  *B23K 26/08* (2014.01)

(52) U.S. Cl.
  CPC .......... *B23K 26/083* (2013.01); *B23K 26/342* (2015.10); *B23K 26/702* (2015.10); *B33Y 10/00* (2014.12); *B33Y 30/00* (2014.12); *B33Y 50/02* (2014.12); *G01N 29/262* (2013.01); *G01N 2291/0231* (2013.01); *G01N 2291/106* (2013.01)

(56) References Cited

U.S. PATENT DOCUMENTS

| | | | |
|---|---|---|---|
| 2007/0176312 A1* | 8/2007 | Clark | B22F 3/1055 264/40.1 |
| 2007/0295440 A1 | 12/2007 | Stucker et al. | |
| 2008/0195003 A1* | 8/2008 | Sliwa | A61N 7/02 601/3 |
| 2013/0228302 A1* | 9/2013 | Rickenbacher | C22C 19/056 164/492 |
| 2014/0163717 A1* | 6/2014 | Das | B22F 3/1055 700/119 |
| 2015/0054191 A1 | 2/2015 | Ljungblad | |

OTHER PUBLICATIONS

EP search report for EP15737649.2 dated Dec. 22, 2016.

* cited by examiner

ADDITIVE MANUFACTURING SYSTEM WITH ULTRASONIC INSPECTION AND METHOD OF OPERATION

This application claims priority to PCT Patent Application No. PCT/US15/011610 filed Jan. 16, 2015 which claims priority to U.S. Patent Application No. 61/928,758 filed Jan. 17, 2014, which are hereby incorporated herein by reference in their entireties.

BACKGROUND

The present disclosure relates to an additive manufacturing system and, more particularly, to an additive manufacturing system with ultrasonic inspection.

Traditional additive manufacturing systems include, for example, Additive Layer Manufacturing (ALM) devices, such as Direct Metal Laser Sintering (DMLS), Selective Laser Melting (SLM), Laser Beam Melting (LBM) and Electron Beam Melting (EBM) that provide for the fabrication of complex metal, alloy, polymer, ceramic and composite structures by the freeform construction of the workpiece, layer-by-layer. The principle behind additive manufacturing processes involves the selective melting of atomized precursor powder beds by a directed energy source, producing the lithographic build-up of the workpiece. The melting of the powder occurs in a small localized region of the energy beam, producing small volumes of melting, called melt pools, followed by rapid solidification, allowing for very precise control of the solidification process in the layer-by-layer fabrication of the workpiece. These devices are directed by three-dimensional geometry solid models developed in Computer Aided Design (CAD) software systems.

The EBM system utilizes an electron beam gun and the DMLS, SLM, and LBM systems utilize a laser as the energy source. Both system beam types are focused by a lens, then deflected by an electromagnetic scanner or rotating mirror so that the energy beam selectively impinges on a powder bed. The EBM system uses a beam of electrons accelerated by an electric potential difference and focused using electromagnetic lenses that selectively scans the powder bed. The DMLS, SLM and LBM utilize a focused laser beam scanned by a rotating mirror. The EBM technology offers higher power densities, and therefore faster scanning rates, over lasers, and is capable of processing superalloys. The powder is melted at the energy focus site on the build surface or substrate. The strategy of the scanning, power of the energy beam, residence time or speed, sequence of melting are directed by an embedded computer aided design system (CAD). The precursor powder is either gravitationally fed from cassettes or loaded by a piston so that it can be raked onto the build table. The excess powder is raked off and collected for re-application. Since the electron gun or laser may be fixed, the build table may lower with each successive layer so that the workpiece is built upon the pre-solidified layer beneath.

Significant effort is needed to improve the speed of ALM processes so that they can become a cost effective option to castings, and to improve the quality because ALM produced work products suffer from several deficiencies resulting in poor material characteristics, such as porosity, melt ball formations, layer delamination, and uncontrolled surface coarseness and material compositions. Moreover, unobtrusive quality control processes that do not add to the manufacturing time or slow down the speed of the ALM processes are lacking.

SUMMARY

An additive manufacturing system according to a non-limiting embodiment of the present disclosure includes an ultrasonic inspection system.

A further embodiment includes a build table for supporting a powder bed, and a sensor array of the ultrasonic inspection system supported by the build table.

A further embodiment of any of the foregoing embodiments includes the sensor array being integrated into the build table.

A further embodiment of any of the foregoing embodiments includes the build table being constructed and arranged to move vertically and the sensor array moving with the build table.

A further embodiment of any of the foregoing embodiments includes a controller having a modeling of a workpiece divided into a plurality of slices and stored electronically, a build table constructed and arranged to move vertically and support a powder bed for the successive manufacture of each slice of the plurality of slices, and an ultrasonic sensor of the ultrasonic inspection system positioned to detect defects in the workpiece as each slice is successively manufactured.

A further embodiment of any of the foregoing embodiments includes the ultrasonic sensor being one of a plurality of ultrasonic sensors forming a sensor array.

A further embodiment of any of the foregoing embodiments includes an ultrasonic inspection software of the ultrasonic inspection system integrated with the controller for firing control of each sensor of the sensor array and processing of ultrasonic data received as electrical signals from the array signifying a material defect in the workpiece.

A further embodiment of any of the foregoing embodiments includes an energy gun controlled by the controller and constructed and arranged to selectively melt a layer of the powder bed associated with each successive slice.

A further embodiment of any of the foregoing embodiments includes the energy gun re-melting at least a portion of a top slice of the plurality of slices to eliminate the material defect and as instructed by the controller.

A further embodiment of any of the foregoing embodiments includes the defect being delamination.

A further embodiment of any of the foregoing embodiments includes the sensor array operating in a phased array mode controlled by the controller for sonic wave activation at variable angles to a top surface of a top slice of the plurality of slices.

A further embodiment of any of the foregoing embodiments includes the sensor array being integrated into the build table.

A further embodiment of any of the foregoing embodiments includes a sheet of the build table having a top face and a bottom face, a bottom slice of the plurality of slices supported directly by the top face, and the sensor array being in direct contact with the bottom face.

A further embodiment of any of the foregoing embodiments includes a transducer and a buffer of each one of the plurality of sensors with the buffer located between the transducer and the bottom face.

A method of operating an additive manufacturing system in another non-limiting embodiment of the present disclosure includes the steps of forming a slice of a workpiece, and performing an ultrasonic inspection of the slice.

A further embodiment of the method includes the further steps of detecting a defect in the workpiece, and re-forming the slice.

A further embodiment of any of the foregoing embodiments includes the further steps of laying a powder bed in a first layer upon a build table, melting at least in-part the first layer into at least one melt pool, and solidifying the melt pool thereby forming the slice as a bottom slice directly upon a build table.

A further embodiment of any of the foregoing embodiments includes the further steps of moving the build table in a downward direction, laying a second layer of the powder bed over the bottom slice, melting at least in-part the second layer into at least one melt pool, solidifying the melt pool thereby forming a top slice disposed over the bottom slice, sending ultrasonic waves through the bottom and top slices, and detecting a defect in the workpiece.

A further embodiment of any of the foregoing embodiments includes the ultrasonic waves in-part reflecting off of a top surface of the top slice and processed by computer software, and in-part reflecting off of a delaminated interface between the top and bottom slices and processed by the computer software to detect the defect.

A further embodiment of any of the foregoing embodiments includes the further step of re-melting the top slice to remove the delamination defect.

The foregoing features and elements may be combined in various combinations without exclusivity, unless expressly indicated otherwise. These features and elements as well as the operation thereof will become more apparent in-light of the following description and the accompanying drawings. It should be understood; however, that the following description and figures are intended to be exemplary in nature and non-limiting.

BRIEF DESCRIPTION OF THE DRAWINGS

Various features will become apparent to those skilled in the art from the following detailed description of the disclosed non-limiting embodiments. The drawings that accompany the detailed description can be briefly described as follows.

DETAILED DESCRIPTION

Figure 1:
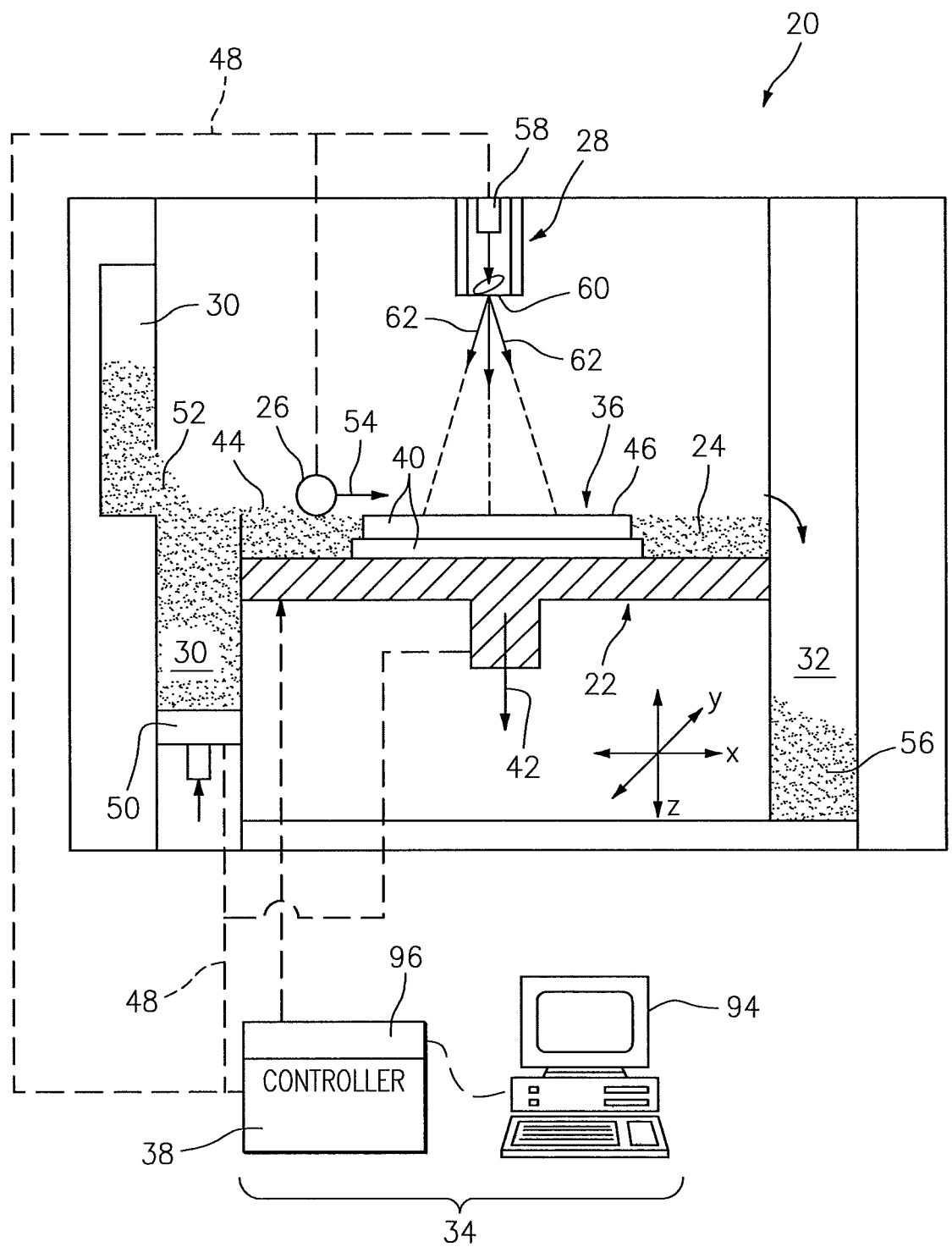
FIG. 1 is a schematic view of an additive manufacturing system according to one non-limiting embodiment of the present disclosure.
Figure 2:
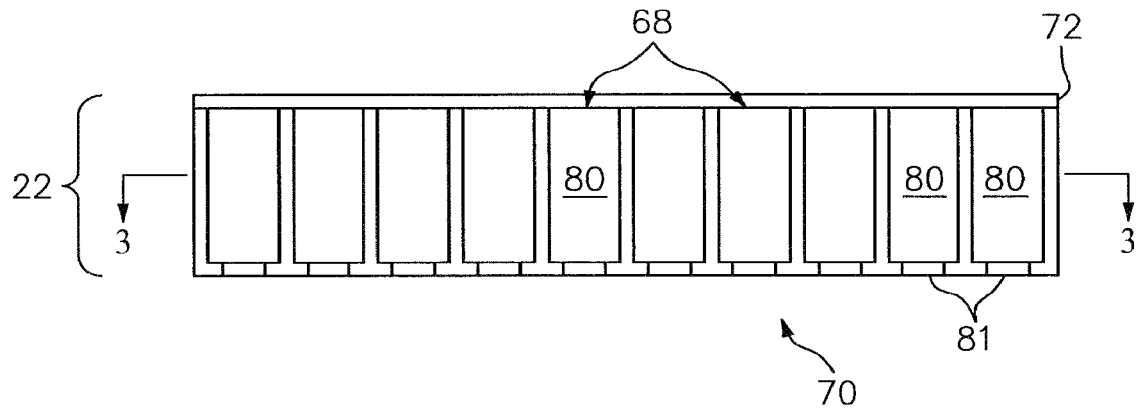
FIG. 2 is a cross sectional side view of a build table of the system.
Figure 3:
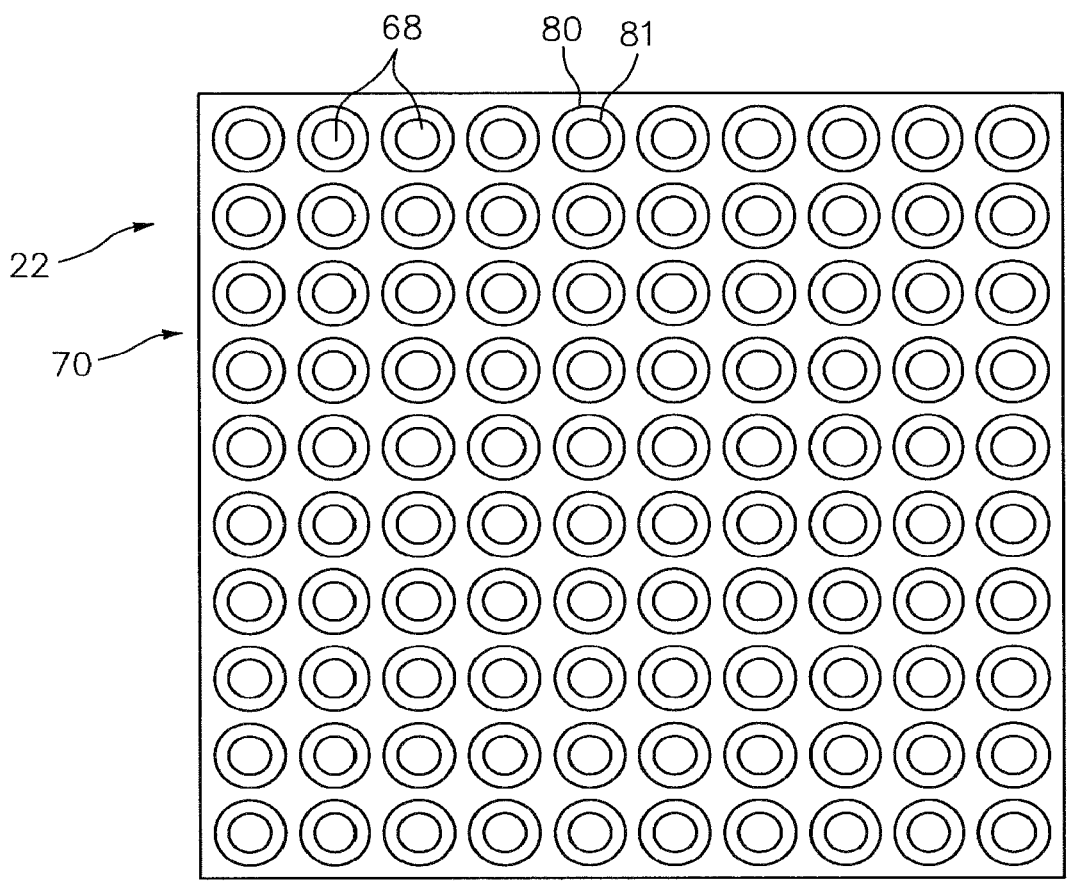
FIG. 3 is a cross section of the build table taken along line 3-3 of FIG. 2.

FIG. 1 schematically illustrates an additive manufacturing system 20 having a build table 22 for holding a powder bed 24, a particle spreader or wiper 26 for spreading the powder bed 24 over the build table, an energy gun 28 for selectively melting regions of a layer of the powder bed, a powder supply hopper 30 for supplying powder to the spreader 26, a powder surplus hopper 32 and an ultrasonic inspection system 34. The additive manufacturing system 20 may be constructed to build a workpiece 36 in a layer-by-layer fashion.

A controller 38 may have an integral CAD system for modeling the workpiece 36 into a plurality of slices 40 additively built atop one-another generally in a vertical or z-coordinate direction (see arrow 42). Once manufactured, each solidified slice 40 corresponds to a layer 44 of the powder bed 24 prior to solidification. The layer 44 is placed on top of a build surface 46 of the previously solidified slice 40. The controller 38 generally operates the entire system through a series of electrical and/or digital signals 48 sent to the system 20 components. For instance, the controller 38 may send a signal 48 to a mechanical piston 50 of the supply hopper 30 to push a supply powder 52 upward for receipt by the spreader 26. The spreader 26 may be a wiper, roller or other device that pushes (see arrow 54) or otherwise places the supply powder 52 over the build surface 46 of the workpiece 38 by a pre-determined thickness established through, downward, movement (see arrow 42) of the build table 22 controlled by the controller 38. Any excess powder 56 may be pushed into the surplus hopper 32 by the spreader 26.

Figure 4:
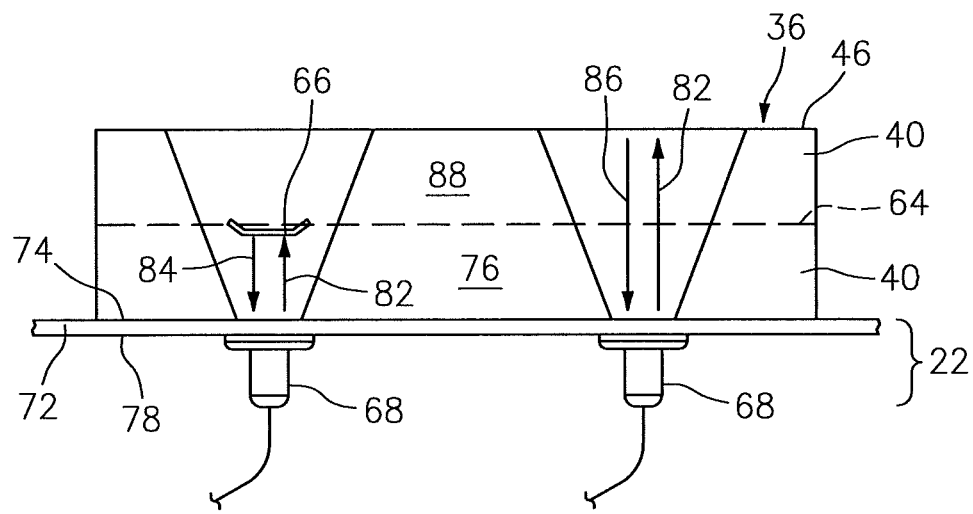
FIG. 4 is a partial enlarged schematic view of the build table and slices of a workpiece and illustrating ultrasonic waves emitted from an ultrasonic array in the table.
Figure 5:
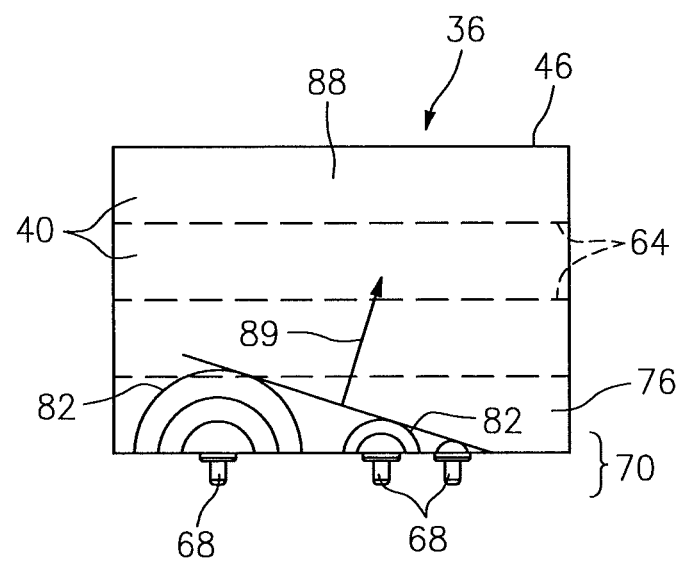
FIG. 5 is a partial enlarged schematic view of the build table and slices of the workpiece and illustrating a sweep angle of ultrasonic waves emitted from an ultrasonic phased array.

Once a substantially level powder layer 44 is established over the build surface 46, the controller 38 may send a signal 48 to the energy gun 28 that energizes a laser or electron beam device 58 and controls a directional mechanism 60 of the gun 28. The directional mechanism 60 may include a focusing lens that focuses a beam (see arrows 62) emitted from device 58 which, in-turn may be deflected by an electromagnetic scanner or rotating mirror of the mechanism 60 so that the energy beam 62 selectively and controllably impinges upon selected regions of the top layer 44 of the powder bed 24. The beam 62 moves along the layer 44 melting region-by-regions of the layer 44 at a controlled rate and power, melting each region into pools that then solidify and ultimately form the slice 40. The process then repeats itself where another powder layer 44 is spread over the last solidified slice 40 and the energy gun 28 melts at least a portion of that layer along with a meltback region of the previously solidified slice 40 to form a uniform and homogeneous interface 64 between slices 40 (also see FIG. 4).

Referring to FIGS. 2 through 5 and during manufacture of the workpiece 36, any number of inconsistencies or defects 66 may inadvertently be created. For instance, defects may include high porosity in the workpiece 36, cracks and delamination between slices 40, amongst other defects. Such may be created by inconsistencies in the powder 30 such as packing or density, undesirable energy gun 38 power or velocity, undesirable solidification rates or thermal gradients across the solidifying slice, and/or any number of other factors. Knowing such defects 66 may inadvertently be formed, the non-destructive, ultrasonic, inspection system 34 is employed and integrated into the additive manufacturing system 20 such that minimal manufacturing interruptions are created and loss of manufacturing time is at a minimum or not lost at all.

The ultrasonic inspection system 34 has a plurality of ultrasonic sensors 68 organized as an array 70 that may be integrated into and moveable with the build table 22. The table 22 has a substantially horizontal sheet 72 having a top face 74 that supports and may be in direct contact with a bottom slice 76 of the plurality of slices 40 of the workpiece 36. An opposite bottom face 78 of the sheet 72 may be in direct contact with a buffer 80 of each sensor 68. Each sensor 68 also has a transducer 81 such that the buffer 80 is located directly between the transducer 81 and the bottom face 78. It is contemplated and understood that the array 70 may not be integrated into the build table 22 and instead may be located anywhere in the system 20 with ultrasonic access to the workpiece and as limited by ultrasonic physics.

The ultrasonic inspection system 34 applies high-frequency sound waves 82 to the workpiece 36 generally each time a slice 40 is fabricated and using one or more of the sensors 68 of the array 70. The sensors 68 or transducers 81 thereof, may include piezocrystal elements that are excited by an electrical voltage to induce the ultrasonic waves 82 in the workpiece 36. When the ultrasonic waves 82 interact with the defect 66, which has a measurable difference in impedance than that of the propagation medium of the workpiece 36, a portion 84 of the ultrasonic wave 82 is either reflected or diffracted back to the originating source. Similarly, a portion 86 of the waves 82 may reflect back from the build surface 46 of a top slice 88 of the plurality of slices 40. This wave portion 86 is also distinctly detectable and thus generally separate from wave portion 84. It is also understood and contemplated that reflected portion 86 may generally not reflect and may instead attenuate through the workpiece as dictated by the characteristics of the build surface 46 (e.g. degree of solidification, coarseness, etc.). By collecting and processing these wave portions or reflections of the waves 82 the integrity of the material of the workpiece can be determined.

The array 70 may be a phased array having individual sensors 68 capable of being pulsed or fired in various quantities, configurations and sequences that allow the ultrasonic energy emitted therefrom to be shaped, angled and/or focused with respect to the workpiece 36. The use of a phased array 70 allows multiple angled beam inspection sweeps to be performed simultaneously. The sweeps performed can be vertical or may be an angled sweep 89 (see FIG. 5) with respect to the z-coordinate. Also, by using additional focal laws, the array can be focused to provide enhanced sensitivity to defects in the workpiece.

The array 70 is in communication with a control device 90 of the ultrasonic inspection system 34 via an electric or digital signal 92 that can be transported through radio transmissions or electrical cable. The device 90 may have a computer 94 and a controller 96 that may be integrated into or part of the controller 38. Regardless both controllers 38, 96 communicate with one another to establish an automated system. The controller 96 is coupled to the computer 94 via electric or digital signals 98 that may be transported through radio transmissions or electrical cable. It is further contemplated and understood that other configurations and combinations may be employed. For instance, the controller 96 may be eliminated and the needed inspection functions can be conducted by the computer 94 with certain parameters inputted to the controller 38.

The controller 96 may be any known phased array control unit capable of being adapted to control the array 70. The computer 94 contains software for programming the controller 96 in accordance with a predetermined set of focal requirements. Accordingly, beam parameters such as angle, focal distance, and focal point that collectively form some of the focal requirements of the array 70 can be entered and modified using the computer 94. The beam parameters entered into the computer 94 are used to program the controller 96 that, in-turn, controls the array 70 to perform the inspection of the workpiece 36. One known, non-limiting, example of a phased array is commercially available under the tradename TomoScan III PA, and one non-limiting example of a controller and/or computer is tradenamed Tomo Scan FOCUS LT both available through the Olympus Corporation, headquartered in Tokyo, Japan and with United States offices in Center Valley, Pa. Additional software may be employed to perform data analysis, and the analyzed results may be sent to the controller 38 instructing the system 20 to either proceed to manufacture the next slice 40 or re-melt the previous slice to remove any detected defects. For example, additive manufactured impellers composed of materials widely used for aerospace applications, such as Aluminum, Nickel and Cobalt base superalloys, may have undesirable internal porosity, voids, lack of fusion, cracks, inclusions, and unmelted particles. The internal defect dimensions can range from submicron to a size comparable to a powder particle size of 50 to 100 microns and beyond.

A powder bed fusion system's controller software can be synchronized with the phased array controller software to initiate a single exposure sequence when a sizable defect is detected at a specific layer. For example, one of the most common defects occurs during scanning of a powder layer utilizing a core and a contour scanning pattern. These two scanning patterns may not overlap each other causing areas with unmelted metal resulting in voids and porosity. In that case the process will not be interrupted and an additional post contour scanning can be utilized in the area where porosity formation was detected.

Figure 6:
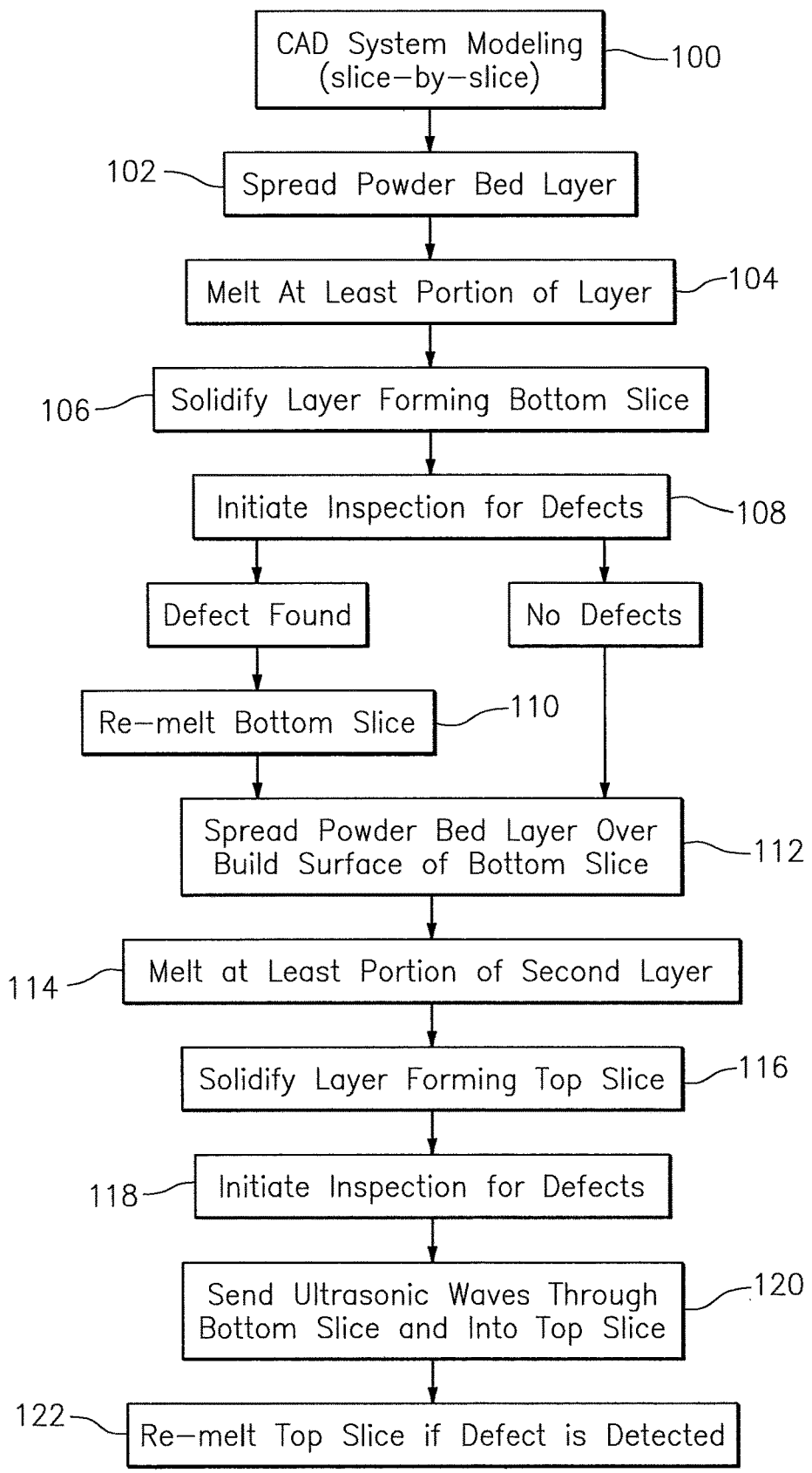
FIG. 6 is a flow chart illustrating a method of operation of the system.

Referring to FIG. 6 and in operation as step 100, a CAD system as part of the controller 38 models the workpiece 36 in a slice-by-slice, stacked orientation. As step 102, a powder bed layer 44 is spread directly over the build table 22 per signals 48 sent from the controller 38. As step 104, the energy gun 28 then melts on a melt pool by melt pool basis a pattern upon the layer 44 mimicking the contour of a bottom slice 76 of the plurality of slices 40 as dictated by the controller 38. As step 106, the melted portion of the powder layer solidifies over a pre-designated time interval thereby completing the formation of a bottom slice 76. As step 108, the controller 38 communicates with the controller 96 of the ultrasonic inspection system 34 and the controller 96 initiates performance of an inspection to detect defects 66 in the bottom slice 76. As step 110 and if a defect is detected, the controllers communicate electronically with one-another and the bottom slice 76 is reformed by re-melting and re-solidification.

As step 112, a powder bed layer 44 is spread over the defect-free bottom slice 76. As step 114, at least a portion of the layer is melted by the energy gun 28 along with a meltback region of the solidified bottom layer 76 in accordance with a CAD pattern of a top slice dictated by the controller 38. As step 116 the melted layer solidifies forming the top slice 88 and a uniform and homogeneous interface 64. As step 118, the controller 38 communicates with the controller 96 and another ultrasonic inspection is initiated sending ultrasonic waves 82 through the bottom slice 76 and into the top slice 88. As step 120, the ultrasonic waves are in-part reflected off of any defects and in-part off of the build surface 46 of the top layer 88, received by the array 70 and processed by computer software. As step 122 and if a defect is detected, such as a delamination defect at the interface 64, the top slice 88 along with the meltback region is re-melted and re-solidified to remove the defects. The system 20 may then repeat itself forming yet additional slices in the same manner described and until the workpiece 36 is completed.

It is understood that relative positional terms such as "forward," "aft," "upper," "lower," "above," "below," and the like are with reference to the normal operational attitude and should not be considered otherwise limiting. It is also understood that like reference numerals identify corresponding or similar elements throughout the several drawings. It should be understood that although a particular component arrangement is disclosed in the illustrated embodiment, other arrangements will also benefit. Although particular step sequences may be shown, described, and claimed, it is understood that steps may be performed in any order, separated or combined unless otherwise indicated and will still benefit from the present disclosure.

The foregoing description is exemplary rather than defined by the limitations described. Various non-limiting embodiments are disclosed; however, one of ordinary skill in the art would recognize that various modifications and variations in light of the above teachings will fall within the scope of the appended claims. It is therefore understood that within the scope of the appended claims, the disclosure may be practiced other than as specifically described. For this reason, the appended claims should be studied to determine true scope and content.

What is claimed is:

1. An additive manufacturing system comprising:
    a build table configured to support a powder bed, the build table having a top side and a bottom side, the build table comprising a sheet defining the top side of the build table, the sheet having a top face and a bottom face; and
    an ultrasonic inspection system comprising a plurality of ultrasonic sensors, the plurality of ultrasonic sensors forming a sensory array integrated into the build table between the top side and the bottom side of the build table;
    wherein the top face is configured to directly support a bottom slice of the plurality of slices and wherein each sensor of the plurality of sensors includes a buffer in direct contact with the bottom face, each buffer located between a respective transducer of each sensor of the plurality of sensors and the bottom face.

2. The additive manufacturing system set forth in claim 1 wherein the build table is constructed and arranged to move vertically and the sensor array moves with the build table.

3. The additive manufacturing system set forth in claim 1 further comprising:
    a controller having a modeling of a workpiece divided into a plurality of slices and stored electronically;
    a build table constructed and arranged to move vertically and support a powder bed for the successive manufacture of each slice of the plurality of slices; and
    an ultrasonic sensor of the ultrasonic inspection system positioned to detect defects in the workpiece as each slice is successively manufactured.

4. The additive manufacturing system set forth in claim 3 further comprising:
    ultrasonic inspection software of the ultrasonic inspection system integrated with the controller for firing control of each sensor of the sensor array and processing of ultrasonic data received as electrical signals from the array signifying a material defect in the workpiece.

5. The additive manufacturing system set forth in claim 4 wherein the sensor array operates in a phased array mode controlled by the controller for sonic wave activation at variable angles to a top surface of a top slice of the plurality of slices.

6. The additive manufacturing system set forth in claim 4 further comprising:
    an energy gun controlled by the controller and constructed and arranged to selectively melt a layer of the powder bed associated with each successive slice.

7. The additive manufacturing system set forth in claim 6 wherein the energy gun is configured to re-melts at least a portion of a top slice of the plurality of slices to eliminate the material defect and as instructed by the controller.

8. The additive manufacturing system set forth in claim 7, wherein the defect is delamination.

* * * * *